United States Patent
Chono et al.

(10) Patent No.: US 11,861,943 B2
(45) Date of Patent: Jan. 2, 2024

(54) IRIS RECOGNITION APPARATUS, IRIS RECOGNITION METHOD, COMPUTER PROGRAM AND RECORDING MEDIUM

(71) Applicant: NEC Corporation, Tokyo (JP)

(72) Inventors: Keiichi Chono, Tokyo (JP); Yuka Ogino, Tokyo (JP); Ryuichi Akashi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 21 days.

(21) Appl. No.: 17/620,797

(22) PCT Filed: Jun. 26, 2019

(86) PCT No.: PCT/JP2019/025344
§ 371 (c)(1),
(2) Date: Dec. 20, 2021

(87) PCT Pub. No.: WO2020/261424
PCT Pub. Date: Dec. 30, 2020

(65) Prior Publication Data
US 2023/0029585 A1 Feb. 2, 2023

(51) Int. Cl.
*G06V 40/18* (2022.01)
*G06V 10/141* (2022.01)

(52) U.S. Cl.
CPC .......... *G06V 40/197* (2022.01); *G06V 10/141* (2022.01)

(58) Field of Classification Search
CPC .... G06V 40/197; G06V 10/141; G06V 40/18; A61B 5/117
See application file for complete search history.

(56) References Cited

U.S. PATENT DOCUMENTS

| 2002/0191076 A1 | 12/2002 | Wada et al. |
| 2003/0020828 A1* | 1/2003 | Ooi ................. G06V 40/18 348/370 |
| 2005/0248725 A1 | 11/2005 | Ikoma et al. |
| 2009/0237208 A1 | 9/2009 | Tsukahara et al. |

(Continued)

FOREIGN PATENT DOCUMENTS

| JP | H10-005195 | 1/1998 |
| JP | 2000-139878 | 5/2000 |

(Continued)

OTHER PUBLICATIONS

Extended European Search Report for EP Application No. EP19934946.5 dated Jun. 9, 2022.

(Continued)

*Primary Examiner* — Syed Haider

(57) ABSTRACT

An iris recognition apparatus is provided with: an irradiating device that is capable of irradiating light to a target person to be recognized; an acquiring device that acquires a first image which imaged a first imaging range including at least a face of the target person; and a determining device that determines an irradiation mode of light irradiated from the irradiating device to the target person when imaging a second image including an area, which includes an eye of the target person, and corresponding to a second imaging range, which is narrower than the first imaging range, based on the first image.

13 Claims, 4 Drawing Sheets

(56) References Cited

U.S. PATENT DOCUMENTS

| | | | | |
|---|---|---|---|---|
| 2014/0133712 A1* | 5/2014 | Boncyk | ............... | G06V 20/20 |
| | | | | 382/117 |
| 2016/0012292 A1* | 1/2016 | Perna | ............... | G06V 40/193 |
| | | | | 382/117 |
| 2016/0253559 A1 | 9/2016 | Goncharov et al. | | |
| 2017/0255823 A1* | 9/2017 | Abe | ............... | A61B 3/10 |
| 2019/0005307 A1* | 1/2019 | Hanna | ............... | G06T 7/521 |

FOREIGN PATENT DOCUMENTS

| | | |
|---|---|---|
| JP | 2002-125142 | 4/2002 |
| JP | 2003-308523 | 10/2003 |
| JP | 2005-304809 | 11/2005 |
| JP | 2006-031185 | 2/2006 |
| JP | 2006-260351 | 9/2006 |
| JP | 2006-330347 | 12/2006 |
| JP | 2007-319174 | 12/2007 |

OTHER PUBLICATIONS

International Search Report for PCT Application No. PCT/JP2019/025344, dated Sep. 17, 2019.

* cited by examiner

IRIS RECOGNITION APPARATUS, IRIS RECOGNITION METHOD, COMPUTER PROGRAM AND RECORDING MEDIUM

This application is a National Stage Entry of PCT/JP2019/025344 filed on Jun. 26, 2019, the contents of all of which are incorporated herein by reference, in their entirety.

TECHNICAL FIELD

This disclosure relates to the technical field of iris recognition apparatus, iris recognition method, computer program and recording medium.

BACKGROUND ART

This type of apparatus requires images with an iris of a target person properly imaged. In some cases, a target person is wearing glasses or the like. In this situation, there is a technical problem that, for example, an iris of a target person may not be properly imaged by imaging reflected light from a lens of an eyeglasses of illumination light. For this problem, for example, an apparatus, which images with two types of illumination that are an illumination suitable for a target person wearing hard contact lenses and an illumination suitable for a target person wearing glasses, has been proposed (see Patent Literature 1). Patent Literatures 2 to 6 are listed as other related technique.

CITATION LIST

Patent Literature

Patent Literature 1: Japanese Patent Application Laid Open No. 2007-319174
Patent Literature 2: Japanese Patent Application Laid Open No. 2006-330347
Patent Literature 3: Japanese Patent Application Laid Open No. 2006-260351
Patent Literature 4: Japanese Patent Application Laid Open No. 2003-308523
Patent Literature 5: Japanese Patent Application Laid Open No. 2000-139878
Patent Literature 6: Japanese Patent Application Laid Open No. H10-005195

SUMMARY

Technical Problem

In the technique described in Patent Document 1, imaging with the above-mentioned two illuminations is performed for all target persons. Therefore, the technique described in Patent Document 1, there is a technical problem that the time required for iris recognition becomes relatively long.

This disclosure has been made in view of the above-mentioned problem. An object of this disclosure is to provide an iris recognition apparatus, an iris recognition method, a computer program, and a recording medium, that can reduce the time required for iris recognition.

Solution to Problem

An aspect of an iris recognition apparatus of this disclosure is provided with: an irradiating device that is capable of irradiating light to a target person to be recognized; an acquiring device that acquires a first image which imaged a first imaging range including at least a face of the target person; and a determining device that determines an irradiation mode of light irradiated from the irradiating device to the target person when imaging a second image including an area, which includes an eye of the target person, and corresponding to a second imaging range, which is narrower than the first imaging range, based on the first image.

An aspect of an iris recognition method of this disclosure includes: acquiring a first image which imaged a first imaging range including at least a face of a target person to be recognized; and determining an irradiation mode of light irradiated to the target person when imaging a second image including an area, which includes an eye of the target person, and corresponding to a second imaging range, which is narrower than the first image range, based on the first image.

An aspect of a computer program of this disclosure causes a computer to execute the one aspect of the iris recognition method as described above.

An aspect of a recording medium of this disclosure is a recording medium in which the one aspect of the computer program as described above is recorded.

Effect

According to one aspect of each of the iris recognition apparatus, iris recognition method, computer program and recording medium as described above, it is possible to reduce the time required for iris recognition.

DESCRIPTION OF EMBODIMENTS

Figure 1:
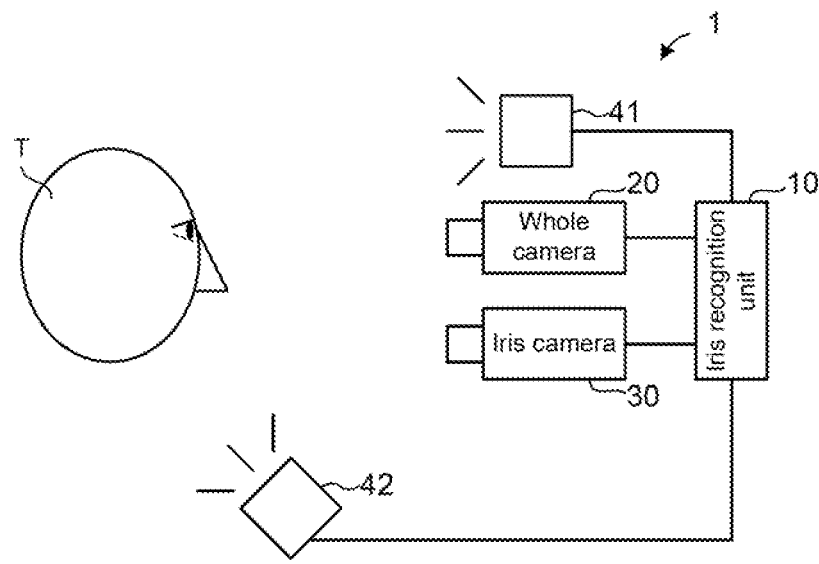
FIG. 1 is a block diagram showing an entire configuration of an iris recognition apparatus of an embodiment.

Embodiments of an iris recognition apparatus, an iris recognition method, a computer program and a recording medium will be described with reference to figures. In the following, embodiments of an iris recognition apparatus, an iris recognition method, a computer program and a recording medium will be described by using an iris recognition apparatus 1 which can perform iris recognition even if a target person wears eyeglasses.
(Configuration)
The entire configuration of the iris recognition apparatus 1 of the embodiment will be described with reference to FIG. 1. FIG. 1 is a block diagram showing the entire configuration of the iris recognition apparatus 1 of the embodiment.

In FIG. 1, the iris recognition apparatus 1 comprises an iris recognition unit 10, a whole camera 20, an iris camera 30, and illumination apparatuses 41 and 42. The whole camera 20 is installed so as to be able to image at least the face of a target person T when the target person T of iris recognition is at a predetermined position (e.g., a position designated by a footprint mark, a position to be seated, etc.). The iris camera is installed so as to be able to suitably image a gaze area, which includes the eye of the target person T, when the target person T is at the predetermined position.

Thereafter, as appropriate, the image imaged by the whole camera 20 is referred to as the "whole image 100", and the image imaged by the iris camera 30 is referred to as the "iris image 200". The resolution of the gaze area in the iris image 200 is higher than the resolution of the gaze area in the whole image 100. In other words, if the image sensor of the whole camera 20 and the image sensor of the iris camera 30 are the same performance, the imaging magnification of the iris camera 30 is higher than the imaging magnification of the whole camera 20. Further, the imaging range of the whole image 100 is wider than the imaging range of the iris image 200. In other words, the imaging range of the iris image 200 is narrower than the imaging range of the whole image 100. The whole image 100 and the iris image 200 correspond to examples of the "first image" and the "second image" in the supplementary note to be described later, respectively. Further, the imaging range of the whole image 100 corresponds to an example of the "first imaging range" in the supplementary note to be described later, and the imaging range of the iris image 200 corresponds to an example of the "second imaging range" in the supplementary note to be described later.

Illumination apparatuses 41 and 42 are installed such that incident angles to the target person T of light to be emitted are different from each other. In particular, the illumination apparatus 42 is installed so as to illuminate the target person T from below the illumination apparatus 41. Illumination apparatuses 41 and 42 may be configured to change other properties of light to be emitted (e.g., at least one of wavelength and intensity). In this embodiment, it is assumed that positional relations and optical features (e.g., an optical axis direction, an angle of view, etc.) of the whole camera 20, the iris camera 30, and the illumination apparatuses 41 and 42 are known. Incidentally, the iris recognition apparatus 1 is not limited to two of the illumination apparatuses 41 and 42 may be provided with three or more illumination apparatuses. Illumination apparatuses 41 and 42 correspond to an example of the "light source" in the supplementary note to be described later.

Figure 2:
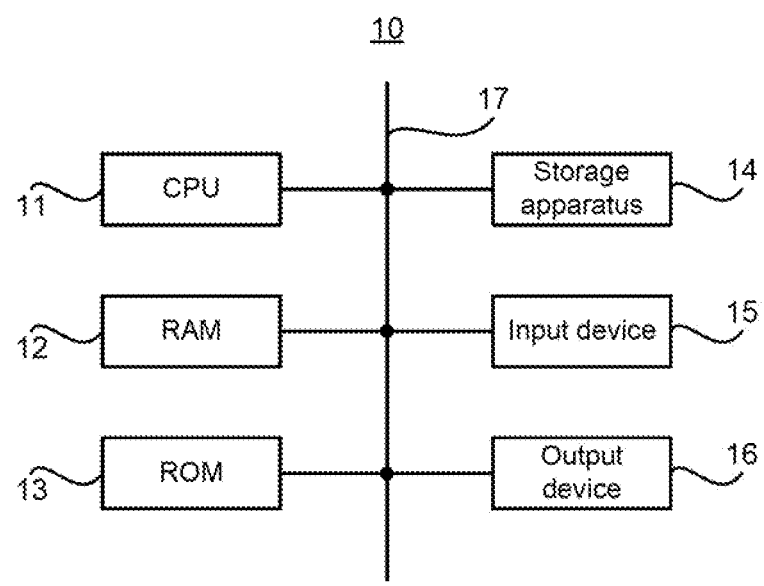
FIG. 2 is a block diagram showing a hardware configuration of an iris recognition unit of the embodiment.

The hardware configuration of the iris recognition unit 10 will be described with reference to FIG. 2. FIG. 2 is a block diagram showing the hardware configuration of the iris recognition unit 10 of the embodiment.

In FIG. 2, the iris recognition unit 10 includes a CPU (Central Processing Unit) 11, a RAM (Random Access Memory) 12, a ROM (Read Only Memory) 13, a storage apparatus 14, an input device 15, and an output device 16. The CPU 11, the RAM 12, the ROM 13, the storage apparatus 14, the input device 15 and the output device 16 are interconnected each other via a data bus 17.

The CPU 11 reads computer programs. For example, the CPU 11 may read a computer program stored by at least one of the RAM 12, the ROM 13 and the storage apparatus 14. For example, the CPU 11 may read a computer program recorded in a computer-readable recording medium using a recording medium reading apparatus not shown. The CPU 11 may acquire (i.e., read) a computer program from an apparatus not shown located outside the iris recognition unit 10 via a network interface.

The CPU 11 controls the RAM 12, the storage apparatus 14, the input device 15 and the output device 16 by executing the read computer program. In particular, in this embodiment, when the CPU 11 executes the read computer program, logical functional blocks for performing iris recognition are realized in the CPU 11. In other words, the CPU 11 can function as a controller for performing iris recognition.

Figure 3:
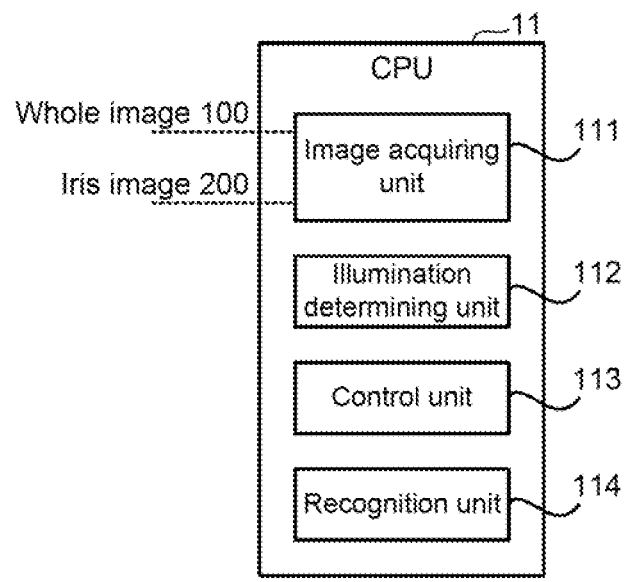
FIG. 3 is a block diagram showing functional blocks implemented in a CPU provided in the iris recognition unit of the embodiment.

In the CPU 11, as shown in FIG. 3, an image acquiring unit 111, an illumination determining unit 112, a control unit 113 and a recognition unit 114 are realized as logical functional blocks. The operation of each of the image acquiring unit 111, the illumination determining unit 112, the control unit 113 and the recognition unit 114 will be described later. Incidentally, the image acquiring unit 111 and the illumination determining unit 112 correspond to examples of the "acquiring means" and the "determining means" in the supplementary note to be described later, respectively. The control unit 113, and illumination apparatuses 41 and 42 correspond to an example of the "irradiation unit" in the supplementary note to be described later.

Returning to FIG. 2, the RAM 12 temporarily stores computer programs executed by the CPU 11. The RAM 12 temporarily stores data that the CPU 11 uses temporarily while the CPU 11 is executing computer programs. The RAM 12 may be, for example, D-RAM (Dynamic RAM).

The ROM 13 stores computer programs executed by the CPU 11. The ROM 13 may store other fixed data. The ROM 13 may be, for example, P-ROM (Programmable ROM).

The storage apparatus 14 stores data that the iris recognition apparatus 1 saves in long-term. The storage apparatus 14 may act as a temporary storage apparatus for the CPU 11. The storage apparatus 14 may include, for example, at least one of a hard disk apparatus, a magneto-optical disk apparatus, an SSD (Solid State Drive) and a disk array apparatus.

The input device 15 is an apparatus that receives input instructions from the user of the iris recognition apparatus 1. The input device 15 may include, for example, at least one of a keyboard, a mouse and a touch panel.

The output device 16 is an apparatus that outputs information about the iris recognition apparatus 1 to the outside. For example, the output device 16 may be a display apparatus capable of displaying information about the iris recognition apparatus 1.

(Operation)

Figure 4:
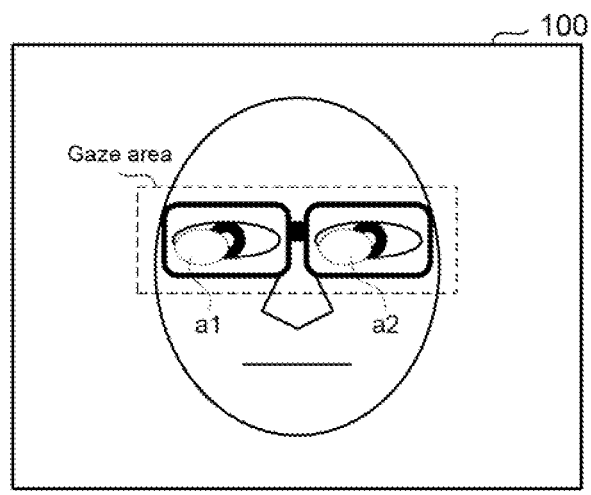
FIG. 4 is an image schematically showing a whole image.

The operation of the iris recognition apparatus 1, which is configured as described above, will be described. First, the operation of the illumination determining unit 112 will be described with reference to FIG. 4. FIG. 4 is a diagram schematically showing the whole image 100. When the target person T wears eyeglasses, the reflected light from the lens of the eyeglasses of the illumination light may be imaged in the whole image 100. In FIG. 4, areas a1 and a2, each of which is surrounded by a dotted line, are portions where the reflected light is imaged. Thereafter, an area corresponding to each of areas a1 and a2 are appropriately referred to as an "illumination reflection area".

The illumination determining unit 112 detects the gaze area (see FIG. 4) by performing a predetermined image processing on the whole image 100. Incidentally, since various existing aspects can be applied to the image processing for detecting the gaze area, a detailed description thereof is omitted. Next, the illumination determining unit 112 detects an area, of which brightness is higher than a predetermined value, as a high-brightness area from the gaze area. Here, the "predetermined value" is a value for determining whether or not an area is the high-brightness area, and is set in advance as a fixed value, or, for example, as a variable value according to an average brightness or the like of the whole image 100. Such the "predetermined value" may be set, for example, as a lower limit of a range, which shows a changeable range of the brightness of the illumination reflection area in the whole image 100 and which is determined experimentally or empirically, or by simulation.

The illumination determining unit 112 identifies, for example, a position, an area, or the like of the detected high-brightness area in the gaze area. Then, the illumination determining unit 112 specifies how much the detected high-brightness area is superimposed on an area corresponding to the iris of the target person T (for example, an area to be estimated as an area, in which the iris is imaged, in the gaze area).

If a degree of superposition of the detected high-brightness area and the area corresponding to the iris of the target person T is a degree such that it does not affect iris recognition, the illumination determining unit 112 determines imaging the iris image 200 by setting the setting of each of illumination apparatuses 41 and 42 to be the same as the setting when the whole image 100 is imaged (i.e., without changing settings). Incidentally, setting items of each of illumination apparatuses 41 and 42 includes, for example, whether or not to light up (in other words, whether or not to emit light), the wavelength of light to be emitted, the intensity of light to be emitted (in other words, brightness), incident angle to the target person T of light to be emitted, etc. Therefore, determining the setting of each of illumination apparatuses 41 and 42 is synonymous with determining light to be illuminated to the target person T (specifically, where, at what angle and what kind of light to be irradiated to the target person T). In other words, determining the setting of each of illumination apparatuses 41 and 42 is synonymous with determining the irradiation mode of light to be irradiated to the target person T.

Here iris recognition will be described briefly. When the iris pattern of a new user is to be registered newly in the iris recognition apparatus 1, the iris pattern of the new user is obtained, for example, as follows: first, an image (corresponding to the iris image 200) including the eye of the new user is imaged, and then a doughnut-shaped iris portion is extracted from the image; next, the doughnut-shaped iris portion is converted into a rectangular image; then, the rectangular image is divided into a plurality of compartments, and then each of the plurality of compartments is quantified (e.g., a representative value of each of the plurality of compartments is determined). Digital data generated by this quantifying correspond to the iris pattern of the new user. Iris recognition is performed by comparing the iris pattern of target person T obtained in the same manner as described above from the iris image 200 with the iris pattern registered in advance in iris recognition apparatus 1. If the degree of coincidence between the two is equal to or greater than a predetermined value, the iris recognition apparatus 1 determines the target person T as a user registered.

A determined result, that whether or not the degree of superposition of the detected high-brightness area and the area corresponding to the iris of the target person T is a degree such that it does not affect iris recognition, varies according to a predetermined value of the above-mentioned degree of the coincidence. For example, the predetermined value is 60%. In this case, if an area, which superimposed with the detected high-brightness area, of the area corresponding to the iris of the target person T is less than 40% of the whole area corresponding to the iris, it can be said that iris recognition is not affected. For example, the predetermined value is 100%. In this case, if the area corresponding to the iris of the target person T and the detected high-brightness area is slightly superimposed, it can be said that iris recognition is affected. The predetermined value may be appropriately set according to, for example, the number of target persons to be recognized of the iris recognition apparatus 1, the recognition accuracy required for the iris recognition apparatus 1, the probability of false recognition estimated from the resolution of the iris image 200, or the like.

On the other hand, when the degree of superposition of the detected high-brightness area and the area corresponding to the iris of the target person T is a degree such that it affects iris recognition, the illumination determining unit 112 sets the setting of each of illumination apparatuses 41 and 42 to a setting, which is different from that when the whole image 100 is imaged. Hereinafter, an exemplary operation, in which the setting of each of illumination apparatuses 41 and 42 is set to a setting, which is different from that when the whole image 100 is imaged, will be described.

The illumination determining section 112 estimates, for example, light, which is emitted from at least one of illumination apparatuses 41 and 42, is reflected at which position of the target person T, and how much light is reflected (i.e., a reflected position and reflected amount of illumination light) on the basis of the position, the area, or the like of the detected high-brightness area in the gaze area, and the setting of each of illumination apparatuses 41 and 42 when the whole image 100 is imaged (in other words, an irradiation information of light irradiated to the target person T).

The illumination determining unit 112 estimates a high-brightness area included in the gaze area in the iris image 200 based on the estimated reflected position and reflected amount of illumination light, and the setting of each of illumination apparatuses 41 and 42. Then, the illumination determining unit 112 determines the setting of each of the illumination apparatuses 41 and 42 such that, for example, the degree of superposition of the high-brightness area and the area corresponding to the iris of the target person T is minimized (or is equal to or less than a predetermined allowable amount) in the iris image 200. At this time, the illumination determining unit 112 particularly determines at least one of the follows: an incident angle of light, which is to be irradiated from one of illumination apparatuses 41 and 42 to the target person T, to the target person T and a wavelength of light, which is to be irradiated from one of illumination apparatuses 41 and 42. The illumination determining unit 112 determines imaging the iris image 200 with the determined setting of each of illumination apparatuses 41 and 42.

Figure 5:
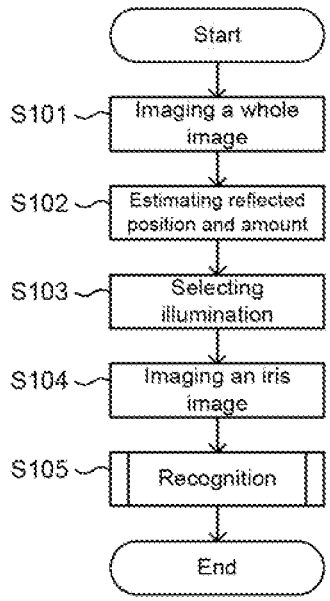
FIG. 5 is a flowchart showing an operation of the iris recognition apparatus of the embodiment.

Next, the operation of the iris recognition apparatus 1 will be described with reference to the flowchart of FIG. 5. In FIG. 5, the control unit 113 sets the setting of each of illumination apparatuses 41 and 42 to the default value (e.g., only the illumination apparatus 41 is lighting), and controls the whole camera 20 so as to image the target person T (step S101).

The illumination determining unit 112 acquires the whole image 100 imaged as a result of the process of the step S101 through the image acquiring unit 111. The illumination determining unit 112 performs the above-described process using the acquired whole image 100. At this time, the illumination determining unit 112 estimates a reflected position and a reflected amount of illumination light if the degree of the superimposition of the high-brightness area detected from the gaze area of the whole image 100 and the area corresponding to the iris of the target person T is the degree such that it does not affect iris recognition (step S102).

Next, the illumination determining unit 112 determines the setting of each of illumination apparatuses 41 and 42 when imaging the iris image 200. In other words, the illumination determining unit 112 selects the illumination when imaging the iris image 200 (step S103).

Next, the control unit 113 sets the setting of each of illumination apparatuses 41 and 42 to the setting determined in the process of the step S103, and controls the iris camera 30 so as to image the target person T (step S104). Thereafter, the recognition unit 114 acquires the iris image 200 imaged as a result of the process of the step S104 through the image acquiring unit 111, and performs a predetermined recognition determination. Since the existing technology can be applied to the recognition determination, a detailed description thereof will be omitted.

Figure 6:
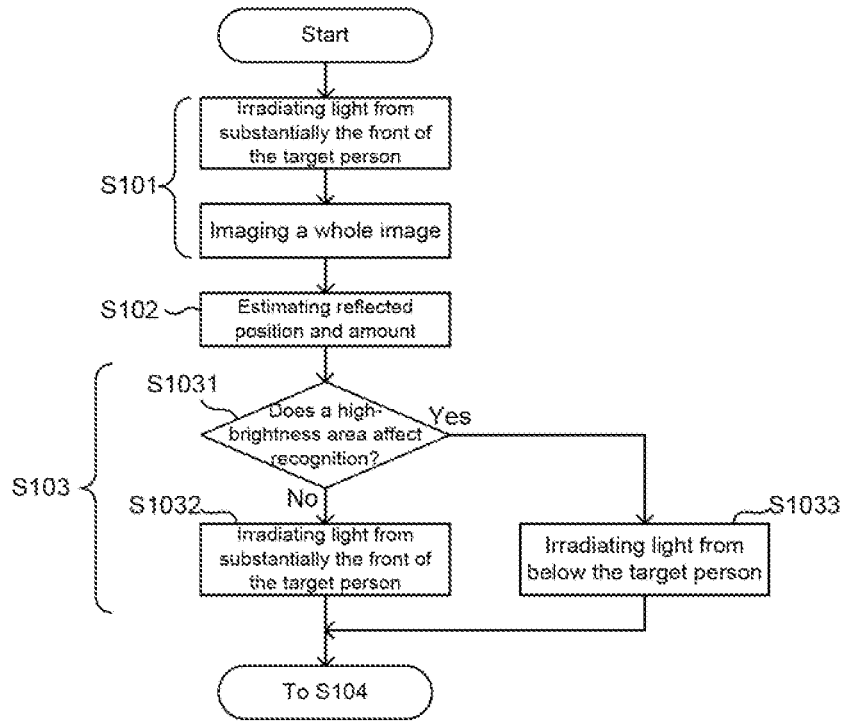
FIG. 6 is a flowchart showing a specific example of the operation of the iris recognition apparatus of the embodiment.

As an example, if the incident angle of light, which is to be irradiated from the illumination apparatus 41, to the target person T and the incident angle of light, which is to be irradiated from the illumination apparatus 42, to the target person T are only different from each other (in other words, other than incident angle, for example, wavelength, intensity, etc. of light are the same in illumination apparatuses 41 and 42), processes of the flowchart of FIG. 5 can be rewritten as shown in FIG. 6. Here, the incident angle of light, which is to be irradiated from the illumination apparatus 41, to the target person T is approximately 0 degrees. In other words, the illumination apparatus 41 illuminates the target person T from substantially the front of the target person T. On the other hand, the illumination apparatus 42 illuminates the target person T from below the face of the target person T. Therefore, the incident angle of light, which is to be irradiated from the illumination apparatus 42, to the target person T differs from the incident angle of light, which is to be irradiated from the illumination apparatus 41, to target person T.

In FIG. 6, the illumination determining unit 112 determines the setting of each of illumination apparatuses 41 and 42 so that light is not irradiated from the illumination apparatus 42 to the target person T while light is irradiated from the illumination apparatus 41 to the target person T when imaging the whole image 100 (in this case, for example, the illumination apparatus 41 is turned on and the illumination apparatus 42 is turned off). The control unit 113 sets illumination apparatuses 41 and 42 according to the determination of the illumination determining unit 112, and controls the whole camera 20 so as to image the target person T (step S101).

After the process of the above-described step S102, the illumination determining unit 112 determines whether or not the degree of the superimposition of the high-brightness area and the area corresponding to the iris of the target person T affects iris recognition (step S1031).

If it is determined that iris recognition is not affected in the process of the step S1013 (Step S1013: No), the illumination determining unit 112 selects the illumination apparatus 41, which is used as the illumination when the whole image 100 is imaged, as the illumination when imaging the iris image 200 (Step S1032). In other words, the illumination determining unit 112 determines that settings of illumination apparatuses 41 and 42 are set to be turned on and not turned on, respectively. Therefore, the target person T is illuminated from its substantially front. In this case, the iris camera 30 images the target person T in which light is not irradiated from the illumination apparatus 42 while light is irradiated from the illumination apparatus 41.

If it is determined that iris recognition is affected in the process of the step S1031 (Step S1031: Yes), the illumination determining unit 112 selects the illumination apparatus 42, which is not used as the illumination when the whole image 100 is imaged, as the illumination when imaging the iris image 200 (Step S1033). In other words, the illumination determining unit 112 determines that settings of illumination apparatuses 41 and 42 are set to be not turned on and set to be turned on, respectively. Therefore, the target person T is illuminated from below its face. In this case, the iris camera 30 images the target person T in which light is not irradiated from the illumination apparatus 41 while light is irradiated from the illumination apparatus 42.

When the iris recognition apparatus 1 includes three or more illumination apparatuses, the illumination determining unit 112 may select one illumination apparatus, which is not used as the illumination apparatus when the whole image 100 is imaged, from a plurality of illumination apparatuses as the illumination apparatus when imaging the iris image 200. At this time, the illumination determining unit 112 may estimate light, which is emitted from each of the plurality of illumination apparatuses, is reflected at which position of the target person T, and how much light is reflected on the basis of the position, the area, or the like of a high-brightness area in a gaze area, and the setting of the illumination apparatus 41 when the whole image 100 is imaged. Thereafter, the illumination determining unit 112 may select one illumination apparatus as the illumination apparatus when imaging the iris image 200 such that, for example, the degree of superposition a high-brightness area and an area corresponding to the iris of the target person T is minimized (or equal to or less than a predetermined allowable amount) in the iris image 200.

Incidentally, considering that the illumination apparatus selected as the illumination apparatus when imaging the iris image 200 irradiates light while the unselected illumination apparatus does not irradiate light, the selection of the illumination apparatus is substantially equivalent to determining irradiating or not irradiating light (i.e., ON/OFF) by each illumination apparatus.

(Technical Effects)

In the iris recognition apparatus 1, the setting of each of illumination apparatuses 41 and 42 when imaging the iris image 200 is determined based on the whole image 100. In other words, in the iris recognition apparatus 1, illumination when imaging the iris image 200 is selected based on the whole image 100. Therefore, the iris recognition apparatus 1 can reduce the time required for iris recognition in comparison with a comparative example which images iris images 200 while sequentially testing a plurality of illumination patterns until the iris image 200, which is suitable for iris recognition, is imaged, for example.

Modification Example (1) The illumination determining unit 112 may determine illumination (e.g., an illumination apparatus to be turned on, an irradiation mode of light to be irradiated from the illumination apparatus to be turned on, etc.) when imaging the iris image 200 based on, for example, a table or the like showing a correspondence between a characteristic (e.g., position, size, etc.) of a high-brightness area, which is detected while light illuminating the target person T by using an illumination apparatus, and an illumination apparatus, which is preferably used as an illumination apparatus when imaging the iris image 200 in that case, instead of obtaining the degree of superimposition of the high-brightness area detected from the gaze area of the whole image 100 and an area corresponding to the iris of the target person T.

(2) At least one of illumination apparatuses 41 and 42 may have a deflecting element (e.g., a movable mirror, etc.), which can change a traveling direction of light in response to an instruction from the control unit 113, on an optical path of light emitted from a light emitting element. Alternatively, at least one of illuminations apparatuses 41 and 42 may have a mechanism, which can change an optical axis in response to an instruction from the control unit 113, (for example, a swing-type illumination apparatus). In these cases, illumination apparatuses 41 and 42 are not needed to be pre-installed so that incident angles of light to be irradiated to the target person T are different from each other.

(3) At least the illumination apparatus 42 may be configured to emit near-infrared light. The illumination determining unit 112 may determine to illuminate the near-infrared light from below the face of the target person T by the illumination apparatus 42 when it is detected from the whole image 100 that the target person T is wearing sunglasses. It has been found by the study of present inventors that the iris of the target person T, who is wearing sunglasses, can be suitably imaged with the above described manner. On the other hand, the illumination determining unit 112 may determine to illuminate the target person T with visible light by at least one of illuminations apparatuses 41 and 42, if the target person T is not wearing glasses, and if the target person T is wearing regular glasses (i.e., non-sunglasses). In other words, in this aspect, a wavelength of light to be irradiated to the target person T may be changed depending on whether or not the target person T is wearing sunglasses.

Figure 7:
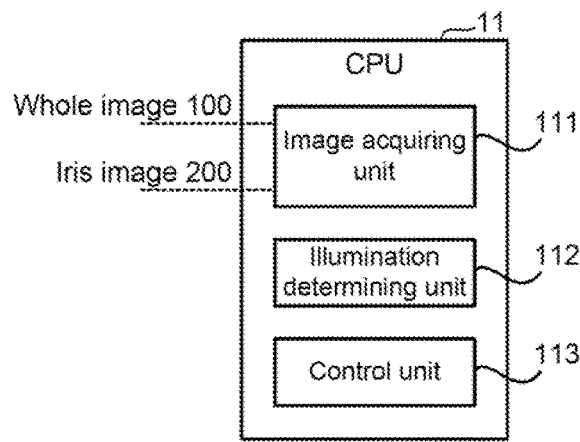
FIG. 7 is a block diagram showing functional blocks implemented in a CPU provided by an iris recognition unit of a modification of the embodiment.

(4) As shown in FIG. 7, the image acquiring unit 111, the illumination determining unit 112 and the control unit 113 are realized in the CPU 11 of the iris recognition unit 10, but function blocks other than the image acquiring unit 111, the illumination determining unit 112 and the control unit 113 are not needed to realize.

(5) an area of a high-brightness area included in the whole image 100 when the target person T is not wearing glasses becomes smaller than that when the target person T is wearing glasses. Because, for example, a reflection amount of illumination light at an eyeball or skin is less than that of illumination light at a lens of eyeglass. Therefore, the illumination determining unit 112 may select illumination, which is the same as illumination when the whole image 100 is imaged, when imaging the iris image 200 if an area of a high-brightness area included in the whole image 100 is less than a predetermined threshold value. The "predetermined threshold value" may be set, for example, as follows: a distribution of an area of a high-brightness area when the target person T is not wearing glasses, and a distribution of an area of a high-brightness area when the target person T is wearing glasses are obtained by experimentally or empirically, or by simulation; then, the predetermined threshold value is set as an area of a high-brightness area when it can be considered that the target person T is not wearing glasses on the basis of obtained distributions.

(6) A glasses detection for the whole image 100 may be performed by applying a pre-existing image processing such as, for example, a pattern matching processing to the whole image 100. The illumination determining unit 112 may select illumination, that is the same as illumination when the whole image 100 is imaged, when imaging the iris image 200 if glasses are not detected (i.e., it is estimated that the target person T is not wearing glasses).

Application Example

Figure 8:
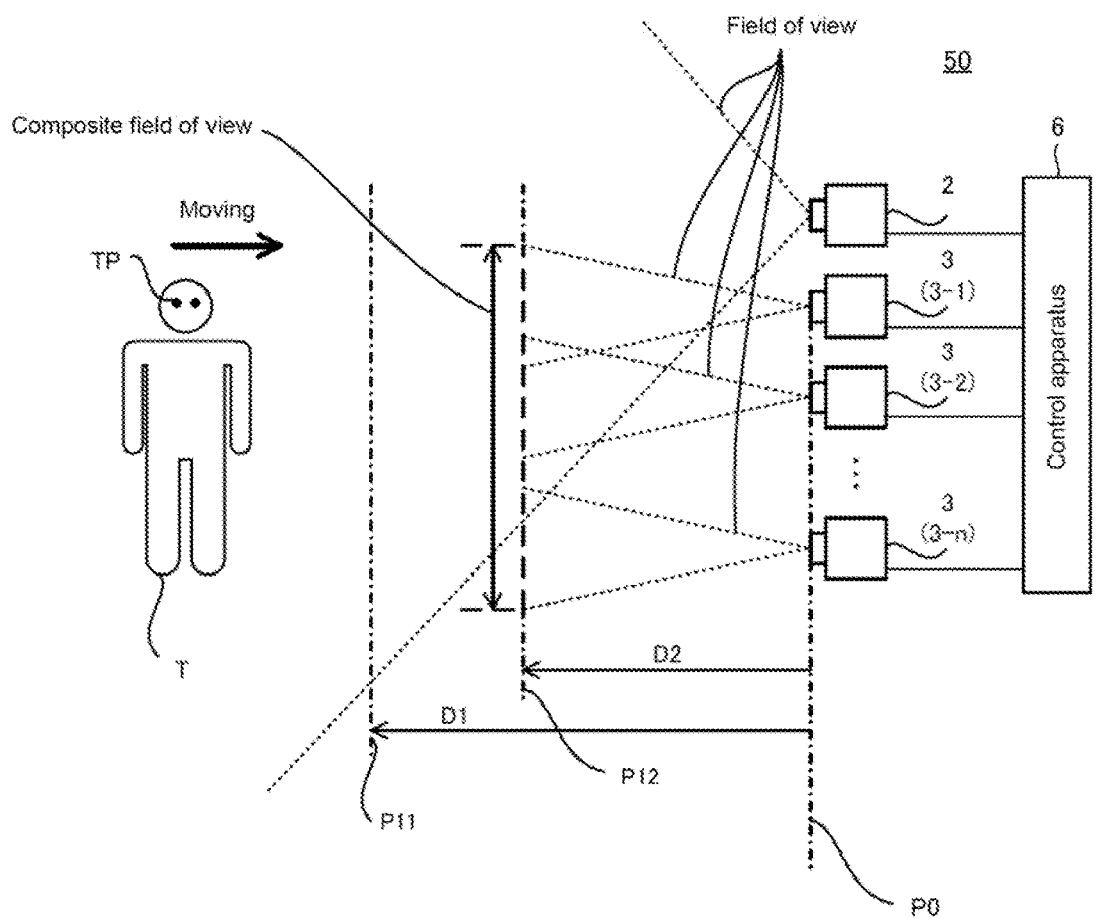
FIG. 8 is a diagram showing a configuration of an iris recognition system of an application example.

The iris recognition apparatus 1 as described above may be employed as a part of the iris recognition system 50 as shown in FIG. 8. The iris recognition system 50 performs an iris recognition operation that performs recognition of the target person T based on an iris pattern of the target person T (e.g., human). The iris recognition system 50 may be employed, for example, as a part of a system for automating entry and exit procedures at airports, so-called ABC (Automated Border Control). In this case, the iris recognition system 50 may be a walk-through type iris recognition system recognizing a moving target person T.

The iris recognition system 50 comprises a whole camera 2, a plurality of iris cameras 3, and a control apparatus 6. The iris recognition unit 10 of the iris recognition apparatus 1 as described above may constitute a part of the control apparatus 6. The whole camera 20 of the iris recognition apparatus 1 as described above may constitute the whole camera 2. The iris camera 30 of the iris recognition apparatus 1 as described above may constitute each of the plurality of iris cameras 3. The whole camera 2 is configured to be capable of imaging the target person T with a field of view, which is wider than the field of view of each of the plurality of iris cameras 3. The "field of view of a camera" means a range that includes a scene that can be imaged by the camera, and may be referred to as an imaging range.

Here, it is assumed that the target person T passes in order of a point P11, a point P12 and a point P0 toward the iris recognition system 50. The distance from the point P0 to the point P11 is the distance D1. The distance from the point P0 to the point P12 is a distance D2, which is shorter than distance D1. The whole camera 2 images the target person T located at the point P11. The control apparatus 6 identifies where a target part TP (corresponding to the "gaze area" as described above) of the target person T is located in the whole image from the whole image imaged by the whole camera 2. Then, the control apparatus 6 determines an iris camera 3, which images the target part TP of the target person T located at the point P12, from the plurality of iris cameras 3. Thereafter, the control apparatus 6 performs recognition of the target person T based on an iris pattern obtained from an iris image imaged by the determined iris camera 3. For more information on the iris recognition system 50, see, for example, Japanese Patent Application Laid Open No. 2019-026937.

<Supplementary Notes>

In regard to the embodiments explained above, the following supplementary notes are further disclosed.

(Supplementary Note 1)

An iris recognition apparatus according to supplementary note 1 is an iris recognition apparatus comprising: an irradiating device that is capable of irradiating light to a target person to be recognized; an acquiring device that acquires a first image which imaged a first imaging range including at least a face of the target person; and a determining device that determines an irradiation mode of light irradiated from the irradiating device to the target person when imaging a second image including an area, which includes an eye of the target person, and corresponding to a second imaging range, which is narrower than the first imaging range, based on the first image.

(Supplementary Note 2)

An iris recognition apparatus according to supplementary note 2 is the iris recognition apparatus according to supplementary note 1, wherein the determining device determines the irradiation mode when imaging the second image based on the first image and an irradiation information of light irradiated to the target person when the first image is imaged.

(Supplementary Note 3)

An iris recognition of apparatus according to supplementary note 3 is the iris recognition apparatus according to supplementary note 2, wherein the determining device determines the irradiation mode when imaging the second image based on a high-brightness area, which is included in an area including the eye of the target person of the first image and of which brightness is higher than a predetermined value, and the irradiation information.

(Supplementary Note 4)

An iris recognition and apparatus according to supplementary note 4, is the iris recognition apparatus according to supplementary note 3, wherein the determining device determines the irradiation mode when imaging the second image by estimating a high-brightness area included in the area of the second image based on the high-brightness area included in the area in the first image, and the irradiation information.

(Supplementary Note 5)

An iris recognition apparatus according to supplementary note 5 is the iris recognition apparatus according to any one of supplementary notes 1 to 4, wherein the determining device determines an incident angle of light irradiated from the irradiating device to the target person as the irradiation mode when imaging the second image, based on the first image.

(Supplementary Note 6)

An iris recognition of apparatus according to supplementary note 6 is the iris recognition apparatus according to supplementary note 5, wherein the irradiating device has a plurality of light sources having different incident angles of light emitted to the target person, and the determining device selects a light source for realizing the determined irradiation mode from the plurality of light sources.

(Supplementary Note 7)

An iris recognition apparatus according to supplementary note 7 is the iris recognition apparatus according to claim 6, wherein the determining device determines an incident angle of light irradiated from the irradiating device to the target person as the irradiation mode when imaging the second image, based on the first image.

(Supplementary Note 8)

An iris recognition apparatus according to supplementary note 8 is the iris recognition apparatus according to any one of supplementary notes 1 to 7, wherein the determining device determines a wavelength of light irradiated from the irradiating device to the target person as the irradiation mode when imaging the second image, based on the first image.

(Supplementary Note 9)

An iris recognition apparatus according to supplementary note 9 is the iris recognition apparatus according to supplementary note 1, wherein the determining device determines imaging the second image with light, which is same as light irradiated from the irradiating device to the target person when the first image is imaged, as the irradiation mode, when an area of a high-brightness area, which is included in an area including an eye of the target person of the first image and of which brightness is higher than a predetermined value, is smaller than a predetermined threshold value.

(Supplementary Note 10)

An iris recognition apparatus according to supplementary note 10 is the iris recognition apparatus according to supplementary note 1, wherein the determining device determines imaging the second image with light, which is same as light irradiated from the irradiating device to the target person when the first image is imaged, as the irradiation mode on a condition that no eyeglasses are detected from the first image.

(Supplementary Note 11)

An iris recognition apparatus according to supplementary note 11 is the iris recognition apparatus according to any one of supplementary notes 1 to 8, wherein the irradiation mode includes at least one of follows: irradiating or not irradiating light by the irradiating device, a traveling direction of light irradiated from the irradiating device to the target person, an optical axis direction of the irradiating device, an incident angle of light irradiated to the target person, and a wavelength of light irradiated to the target person.

(Supplementary Note 12)

An iris recognition method according to supplementary note 12 is an iris recognition method comprising: acquiring a first image which imaged a first imaging range including at least a face of a target person to be recognized; and determining an irradiation mode of light irradiated to the target person when imaging a second image including an area, which includes an eye of the target person, and corresponding to a second imaging range, which is narrower than the first image range, based on the first image.

(Supplementary Note 13)

A computer program according to supplementary note 13 is a computer program for causing a computer to execute the iris recognition method according to supplementary note 12.

(Supplementary Note 14)

A recording medium according to supplementary note 14 is a recording medium on which the computer program according to supplementary note 13 is recorded.

This disclosure can be modified as appropriate in a range not contrary to the claimed range and the subject matter or philosophy of this disclosure which can be read from the entire specification, and iris recognition apparatuses, iris recognition methods, computer programs and recording media with such modifications are also included in the technical philosophy of this disclosure.

DESCRIPTION OF REFERENCE NUMERALS AND LETTERS

1 . . . iris recognition apparatus
10 . . . iris recognition unit
20 . . . whole camera
30 . . . iris camera
111 . . . image acquiring unit
112 . . . illumination determining unit
113 . . . control unit
114 . . . recognition unit

What is claimed is:

1. An iris recognition apparatus comprising:
a light source configured to irradiate a target person to be recognized with light;
a camera;
one or more processors; and
a memory storing program code executable by the one or more processors to:
cause the camera to acquire a first image at a first imaging range, including at least a face of the target person, while the target person is irradiated with the light by the light source;
determine, based on the first image, an irradiation mode of the light for acquiring a second image at a second imaging range narrower than the first imaging range, including an eye of the target person;

cause the light source to irradiate the target person with the light according to the irradiation mode that has been determined; and cause the camera to acquire the second image at the second imaging range, including at least the eye of the target person, while the target person is irradiated with the light by the light source according to the irradiation mode that has been determined, wherein the irradiation mode of the light for acquiring the second image is set as equal to an irradiation mode of the light with which the target person was irradiated when the camera acquired the first image when no eyeglasses are detected within the first image.

2. The iris recognition apparatus according to claim 1, wherein the irradiation mode is determined further based on an irradiation information of the light with which the target person was irradiated when the camera acquired the first image at the first imaging range.

3. The iris recognition apparatus according to claim 2, wherein the irradiation mode is determined further based on an area of the first image including the eye of the target person having a brightness higher than a predetermined value.

4. The iris recognition apparatus according to claim 3, wherein the irradiation mode is determined by estimating, prior to acquisition of the second image, a brightness of an area of the second image including the eye of the target person, based on the brightness of the area of the first image including the eye of the target person, and based on the irradiation information.

5. The iris recognition apparatus according to claim 1, wherein the program code is executable by the one or more processors to further determine an incident angle of the light for acquiring the second image, based on the first image.

6. The iris recognition apparatus according to claim 1, wherein
the light source is one of a plurality of light sources having different incident angles of the light relative to the target person, and
the program code is executable by the one or more processors to further selects the light source to cause to irradiate the target person with the light according to the irradiation mode that has been determined, from the plurality of light sources.

7. The iris recognition apparatus according to claim 6, wherein the program code is executable by the one or more processors to further determine an incident angle of the light for acquiring the second image, based on the first image.

8. The iris recognition apparatus according to claim 1, wherein the program code is executable by the one or more processors to further determine a wavelength of the light for acquiring the second image, based on the first image.

9. The iris recognition apparatus according to claim 1, wherein the irradiation mode of the light for acquiring the second image is set as equal to an irradiation mode of the light with which the target person was irradiated when the camera acquired the first image when a portion of an area of the first image including the eye of the target person having a brightness higher than a predetermined value is smaller than a predetermined threshold value.

10. The iris recognition apparatus according to claim 1, wherein the irradiation mode includes one or more of the following: a traveling direction of the light, an incident angle of the light relative to the target person, and a wavelength of the light.

11. An iris recognition method comprising:
causing a camera to acquire a first image at a first imaging range, including at least a face of a target person to be recognized, while the target person is irradiated with light by a light source;
determining, based on the first image, an irradiation mode of the light for acquiring a second image at a second imaging range narrower than the first imaging range, including an eye of the target person;
causing the light source to irradiate the target person with the light according to the irradiation mode that has been determined; and
causing the camera to acquire the second image at the second imaging range, including at least the eye of the target person, while the target person is irradiated with the light by the light source according to the irradiation mode that has been determined,
wherein the irradiation mode of the light for acquiring the second image is set as equal to an irradiation mode of the light with which the target person was irradiated when the camera acquired the first image when no eyeglasses are detected within the first image.

12. A non-transitory recording medium storing a computer program executable by to perform processing comprising:
causing a camera to acquire a first image at a first imaging range, including at least a face of a target person to be recognized, while the target person is irradiated with light by a light source;
determining, based on the first image, an irradiation mode of the light for acquiring a second image at a second imaging range narrower than the first imaging range, including an eye of the target person;
causing the light source to irradiate the target person with the light according to the irradiation mode that has been determined; and
causing the camera to acquire the second image at the second imaging range, including at least the eye of the target person, while the target person is irradiated with the light by the light source according to the irradiation mode that has been determined,
wherein the irradiation mode of the light for acquiring the second image is set as equal to an irradiation mode of the light with which the target person was irradiated when the camera acquired the first image when no eyeglasses are detected within the first image.

13. The iris recognition apparatus according to claim 1, wherein the irradiation mode of the light for acquiring the second image is set as equal to an irradiation mode of the light with which the target person was irradiated when the camera acquired the first image when a portion of an area of the first image including the eye of the target person having a brightness higher than a predetermined value has a degree of superposition with an iris area of the target person less than or equal to a predetermined degree.

* * * * *